(12) United States Patent
Shahinpoor et al.

(10) Patent No.: US 9,681,945 B2
(45) Date of Patent: Jun. 20, 2017

(54) DOUBLE ACCOMMODATING INTRAOCULAR ACCORDION LENS

(71) Applicants: Mohsen Shahinpoor, Bangor, ME (US); David P. Soltanpour, Larchmont, NY (US)

(72) Inventors: Mohsen Shahinpoor, Bangor, ME (US); David P. Soltanpour, Larchmont, NY (US)

(*) Notice: Subject to any disclaimer, the term of this patent is extended or adjusted under 35 U.S.C. 154(b) by 36 days.

(21) Appl. No.: 14/854,323

(22) Filed: Sep. 15, 2015

(65) Prior Publication Data
US 2017/0071728 A1    Mar. 16, 2017

(51) Int. Cl.
*A61F 2/16* (2006.01)

(52) U.S. Cl.
CPC .......... *A61F 2/1624* (2013.01); *A61F 2/1629* (2013.01); *A61F 2/1635* (2013.01); *A61F 2/1648* (2013.01); *A61F 2002/1682* (2015.04)

(58) Field of Classification Search
CPC .... A61F 2/1613; A61F 2/1624; A61F 2/1629; A61F 2/1632; A61F 2/1635; A61F 2/1682
See application file for complete search history.

(56) References Cited

U.S. PATENT DOCUMENTS

| 7,060,094 B2 | 6/2006 | Shahinpoor et al. |
| 8,048,155 B2 | 11/2011 | Shadduck |
| 8,123,803 B2 | 2/2012 | Shaninpoor et al. |
| 9,011,532 B2 | 4/2015 | Bumbalough et al. |
| 9,072,599 B2 | 7/2015 | Kadziauskas et al. |
| 2004/0111153 A1* | 6/2004 | Woods ............... A61F 2/1613 623/6.37 |
| 2015/0173892 A1 | 6/2015 | Borja et al. |
| 2015/0182327 A1 | 7/2015 | Cumming |
| 2015/0182328 A1 | 7/2015 | Cumming |

* cited by examiner

*Primary Examiner* — Howie Matthews
(74) *Attorney, Agent, or Firm* — Dennis F. Armijo

(57) ABSTRACT

A Double Accommodating Intraocular Lens (DAIOL), which not only axially moves its flexible optic to accommodate, but also peripherally compresses or decompresses the optic to change its convexity or power, thus, double accommodating simultaneously upon contraction or expansion of the ciliary muscles and subsequently the lens capsule. The DAIOL includes a deployable semi-rigid or elastic haptic assembly and a flexible single optic. The DAIOL is further composed of three or four ring haptics and three or four deployable resilient lazy tongs, attached to a single elastically flexible plate encompassing a flexible optic. Accordingly, the radial compression of the capsular bag by the contraction of the ciliary muscles axially moves and radially compresses the flexible optic in the lens and vice versa upon radial expansion of the capsular bag, backward axial movement, and decompression of the optic, due to the resilient lazy tongs action, for double accommodation.

10 Claims, 15 Drawing Sheets

DOUBLE ACCOMMODATING INTRAOCULAR ACCORDION LENS

BACKGROUND OF THE INVENTION

Field of the Invention (Technical Field)

The presently claimed invention relates to Intraocular Lenses (IOLs) and, more particularly to Double Accommodating Intraocular Accordion Lenses (DAIOLs) with deployable semi-rigid elastic haptics to deploy within the lens capsule, axially move, and radially compress a soft single optic.

Background Art

This state of the art has a very long background in terms of surgical replacement of a cataractous lens by an intraocular artificial lens. The majority of these surgical operations are performed by capsulorhexis and phacoemulsification. In a typical procedure, an opening is made in the anterior capsule by a cystotome and a thin phacoemulsification cutting tip is inserted into the diseased lens. The lens is ultrasonically vibrated to emulsify and liquefy the cataractous lens and aspirate it out of the lens capsular bag. A very thorough discussion of the state of the art is disclosed in U.S. Pat. No. 9,011,532 B2 to Bumbalough, et al., and this discussion is incorporated as if fully set forth herein. In Bumbalough, "an intraocular lens is disclosed, with an optic that changes shape in response to a deforming force exerted by the zonules of the eye. A haptic supports the optic around its equator and couples the optic to the capsular bag of the eye. Certain haptic features improve the accommodative performance of the haptic, such that compressive/tensile forces may be more efficiently transferred from the haptic to optic. Furthermore, certain aspects also provide enhanced bag-sizing capability so that the IOL better fits within the capsular bag". Bumbalough clearly indicates the importance of IOLs and DAIOLs because a cataract is such a common disease and cataract surgery is necessary. Other related prior art includes the following:

U.S. Pat. No. 9,072,599 to Kadziauskas, et al., discusses "an accommodating intraocular lens (aIOL) is disclosed, with an optic that changes shape in response to an ocular force exerted by the zonules of the eye. A haptic supports the optic around its equator and couples the optic to the capsular bag of the eye. A surface adherent improves the accommodative performance of the haptic, such that compressive/tensile forces may be more efficiently transferred from the haptic to optic. One way to enhance force transfer is to provide a surface layer of an adhesive to the haptic and/or optic, for instance a reversible bioadhesive material. Alternatively, portions of the exterior surface of the IOL may have microfibers thereon that mimic the adhesive properties of Gecko feet. Another aspect is application of a reversible bioadhesive material to the interior of the empty capsular bag prior to introduction of an injectable polymer IOL".

U.S. Patent Application No. 2015/0173892 to Borja, et al., discloses "an accommodating intraocular lens includes a haptic assembly and a flexible optic. The haptic assembly includes an anterior ring, a posterior ring, anterior spring arms, and posterior spring arms, wherein the anterior spring arms and the posterior spring arms bias the anterior ring and the posterior ring apart from one another. The flexible optic is suspended between the anterior ring and the posterior ring and connected to the haptic assembly by a plurality of support struts. The support struts are adapted to deform the flexible optic upon axial compression of the haptic assembly so that an optical power of the flexible optic is reduced relative to an uncompressed state of the haptic assembly".

U.S. Patent Application No. 2015/0182327 to Cumming, states "a non-accommodating intraocular lens comprises a flexible optic and at least one haptic connected to the optic. The at least one haptic comprises a rigid structure".

U.S. Patent Application No. 2015/0182328 to Cumming, introduces "an intraocular lens having a single-focus, acrylic optic and at least one semi-rigid, acrylic haptic connected to the optic. The intraocular lens can have a fixed longitudinal length, e.g., the same fixed length pre-operatively and post-operatively. The intraocular lens can resist deformation, despite contraction and relaxation of the ciliary muscle and fibrosis within the capsular bag, after implantation into the eye using, for example, by the semi-rigid haptics. The intraocular lens can be sufficiently flexible to be compressed from an original configuration to a compressed configuration for insertion into the eye through a small incision and return to the original configuration after implantation into the eye".

U.S. Pat. No. 8,048,155 to Shadduck, discusses "a deformable intracapsular implant device for shaping an enucleated lens capsule sac for use in cataract procedures and refractive lensectomy procedures. In one embodiment, the intraocular implant devices rely on thin film shape memory alloys and combine with the post-phaco capsular sac to provide a biomimetic complex that can mimic the energy-absorbing and energy-releasing characteristics of a young accommodative lens capsule. In another embodiment, the capsular shaping body is combined with an adaptive optic. The peripheral capsular shaping body carries at least one fluid-filled interior chamber that communicates with a space in an adaptive optic portion that has a deformable lens surface. The flexing of the peripheral shaping body in response to zonular tensioning and de-tensioning provides an inventive adaptive optics mechanism wherein fluid media flows between the respective chambers 'adapts' the optic to increase and decrease the power thereof. In one embodiment, the capsular shaping body carries a posterior negative power adaptive optic that can be altered in power during accommodation to cooperate with an independent drop-in exchangeable intraocular lens".

U.S. Pat. No. 8,123,803 to Shahinpoor, et al., discusses "an ophthalmic device and system of mounting for correcting hyperopia and presbyopia. The presently claimed invention includes a limbus ring mountable in an encircling relation to a central optic zone of a cornea on a limbus annulus surrounding the cornea. In the limbus ring defines a substantially annular toroid defining a first average diameter that is selectable and has a hydrophilic coating disposed thereon. The inner radius of the limbus ring is selectable such that, upon mounting on the limbus annulus, the limbus ring causes the limbus annulus to contract thereby causing the curvature of the cornea and the eye length to increase. The mounting system of the presently claimed invention is adapted to receive a limbus ring and further adapted to selectively place the limbus ring on a limbus annulus".

U.S. Pat. No. 7,060,094 to Shahinpoor, et al., discloses a "surgical correction of presbyopia and hyperopia by a circularly distributed assembly of mini-bridges implanted between the interior surfaces of the ciliary muscle and the exterior surface of the lens capsule, for augmenting the transmission of the contraction force of the ciliary muscle/zonule assembly to the lens capsule. The lens is symmetrically squeezed by mini-bridges acting in concert with the ciliary muscle thus changing the curvature of the lens. The mini-bridges are composite synthetic muscles comprising either passive biocompatible mini-bridges made with polymeric gels, silicone polymers or a composite, electromagnetically or mechanically deployable mini-bridges, inflatable balloons or synthetic muscles. The surgical procedure comprises using a ciliary muscle relaxant to stretch the lens/zonules/ciliary muscle assembly. An Ultrasonic Biomicroscope (UBM) is then used to enable the surgeon to see the area for implantation and the mini-bridges and thus perform endoscopic or incisional surgery to implant the mini-bridges in and around zonular cavities." It is important to note that as discussed in the '094 patent, the ciliary muscles push the stiff zonular fibers on to the edge or equator of the natural lens capsular bag to change the shape of the lens and thus accommodate for near and far images. This mechanism is known as accommodation. The natural lens, which is contained within a transparent capsule, is soft, early in life. The bag is suspended by the zonules attached with the ciliary muscles. Accommodation allows the natural lens to focus alternatively on near and far objects.

With age, various eye diseases occur that impair a person's vision. For instance, a cataract may increase the opacity of the lens, causing partial or complete blindness. In order to restore the patient's vision, the diseased lens should be surgically removed and replaced with an artificial lens, known as an intraocular lens, or IOL. With time, and as the lens ages, it becomes unable to fully accommodate due a number of reasons including stiffening to change its shape in reaction to the tightening of the ciliary muscles. This makes it harder for the lens to focus on near objects, a medical condition known as presbyopia. A DAIOL may also be used to correct presbyopia.

SUMMARY OF THE INVENTION

Disclosure of the Invention

The presently claimed invention solves the ongoing problems addressed above by providing double accommodating IOLs (DAIOLs) with deployable semi-rigid elastic haptics and resilient lazy tongs to deploy within the lens capsule, and axially move and peripherally compress a plate encompassing a soft single optic. The resilient lazy tongs resiliently deploy back when the peripheral capsular pressure due to contraction of the ciliary muscles is gone. The deployment of the resilient lazy tongs produces axial movement of the plate encompassing the soft optic, produces radial compression of the optic due to resilient lazy tongs lateral inward deployment, and peripherally compresses the plate.

The presently claimed invention is an accommodating intraocular lens structure made with biocompatible materials such as polymeric acrylics, collamer, silicones, and soft biocompatible polymeric materials such as Polydimethylsiloxane (PDMS) and semi-rigid elastic materials such as Poly Methyl Methacrylate (PMMA) and placed inside the eye capsule during cataract surgery. The preferred embodiment includes a deployable semi-rigid or elastic haptic assembly and a flexible single optic. The semi-rigid haptic assembly preferably includes three or four ring haptics and three or four deployable resilient lazy tongs, like a single cell scissor-like lazy tong or accordion structures. These structures are attached to a single elastically flexible plate encompassing a flexible optic. This configuration provides for radial compression of the capsular bag by the contraction of the ciliary muscles, and axially moves and radially compresses the flexible optic in the lens. This also provides radial expansion of the capsular bag and backward axial movement and decompression of the optic, due to the x-tongs action, for double accommodations. The flexible optic is suspended and connected to the deployable lazy tong haptic assembly by a plurality of three or four single cell lazy tong units. The lazy tong double accommodating intraocular lens is sufficiently flexible to be compressed for insertion into the eye through a small incision and snap back to the original configuration after implantation into the capsular bag of the eye.

It is important to address a number of challenges in implementing an accommodating optic. One important challenge is designing a suitable haptic to couple the optic to the capsular bag during surgery. The design of the elastic haptics should be such that they can easily allow accommodative movement and distortion of the optic in an efficient manner. Thus, a relatively small ocular force from the ciliary muscle, zonules, and/or capsular bag is capable of producing a relatively large change in power and/or axial location of the image. The presently claimed invention accomplishes these goals.

A primary object of the presently claimed invention is to provide a double accommodating intraocular lens for patients undergoing cataract surgery or patients desiring to correct their presbyopia.

A primary advantage of the presently claimed invention is that it provides double accommodating action and thus may produce more than five (5) or six (6) diopters of power for accommodation.

Other objects, advantages and novel features, and further scope of applicability of the presently claimed invention will be set forth in part in the detailed description to follow, taken in conjunction with the accompanying drawings, and in part will become apparent to those skilled in the art upon examination of the following, or may be learned by practice of the presently claimed invention. The objects and advantages of the presently claimed invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the presently claimed invention and, together with the description, serve to explain the principles of the presently claimed invention. The drawings are only for the purpose of illustrating a preferred embodiment of the presently claimed invention and are not to be construed as limiting the presently claimed invention. In the drawings:

FIG. 17b depicts the top view line drawing of the accordion double accommodating intraocular lens of FIG. 17a.

FIG. 18 depicts the perspective side view of the accordion double accommodating intraocular lens of FIG. 17a.

FIG. 22b Illustrates the line drawing of the top perspective view of the accordion double accommodating intraocular lens of FIG. 22a.

DESCRIPTION OF THE PREFERRED EMBODIMENTS

Best Modes for Carrying Out the Invention

Generally, in a healthy human eye, the compression and expansion of the capsular bag distorts the natural lens in order to change its power and/or the location of the lens. This capsular deformation enables the eye to focus on objects at varying distances away from the eye in a process known as accommodation. For some people who develop cataractous lenses, the natural lens of the eye becomes clouded or opaque. A standard treatment is lens replacement by capsulorhexis and phacoemulsification in a cataract surgery, during which the natural lens is ultrasonically fragmented, removed, and replaced with a manufactured intraocular lens. Typically, the capsular bag with an opening is left in the eye during the surgery to house the implanted intraocular lens.

Since the capsular bag is compressed or expanded by the action of the ciliary muscles and zonular fibers, it is desirable to have specially designed mechanisms to allow the motion of the capsular bags to be transmitted to the implanted intraocular lens to change its power and/or location in the eye in a manner similar to that of the natural lens. The deployable lazy tong mechanism upon reacting to the squeezing or expanding radial force applied largely to the elastic haptics not only moves the lens in its axial direction, but also squeezes the lens and slightly bulges it up in the axial direction due to reaction forces of the lazy tong, thus, producing double accommodation both in moving the lens axially as well as making it more powerful by squeezing it. This disclosure describes a first embodiment comprising a deployable semi-rigid or elastic haptic assembly and a flexible single optic. An alternative embodiment that comprises a dual optic assembly is also disclosed.

Figure 1A:
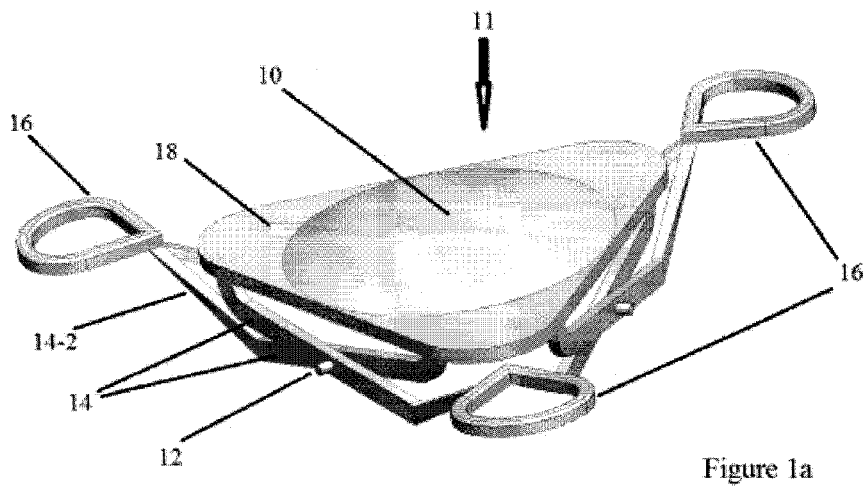
FIG. 1a illustrates the top perspective view of the preferred accordion double accommodating intraocular lens.
Figure 1B:
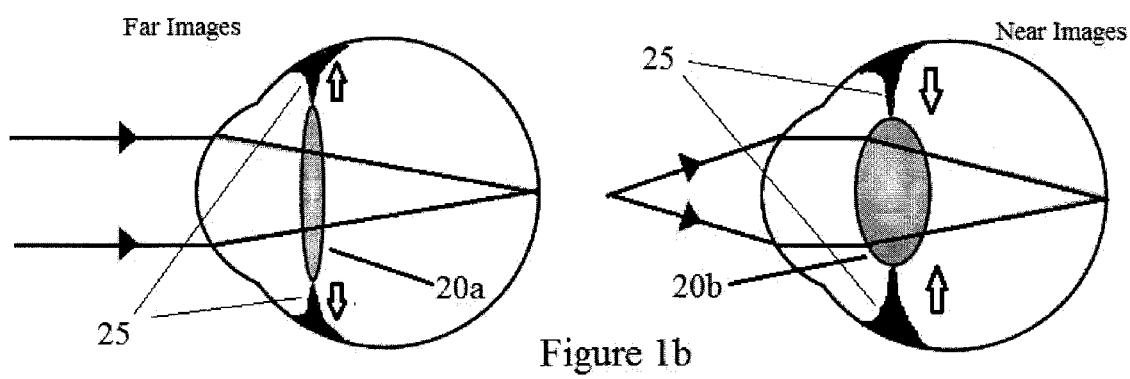
FIG. 1b illustrates the essence of accommodation by the natural lens due to the splintering or relaxation actions of the ciliary muscles.
Figure 1C:
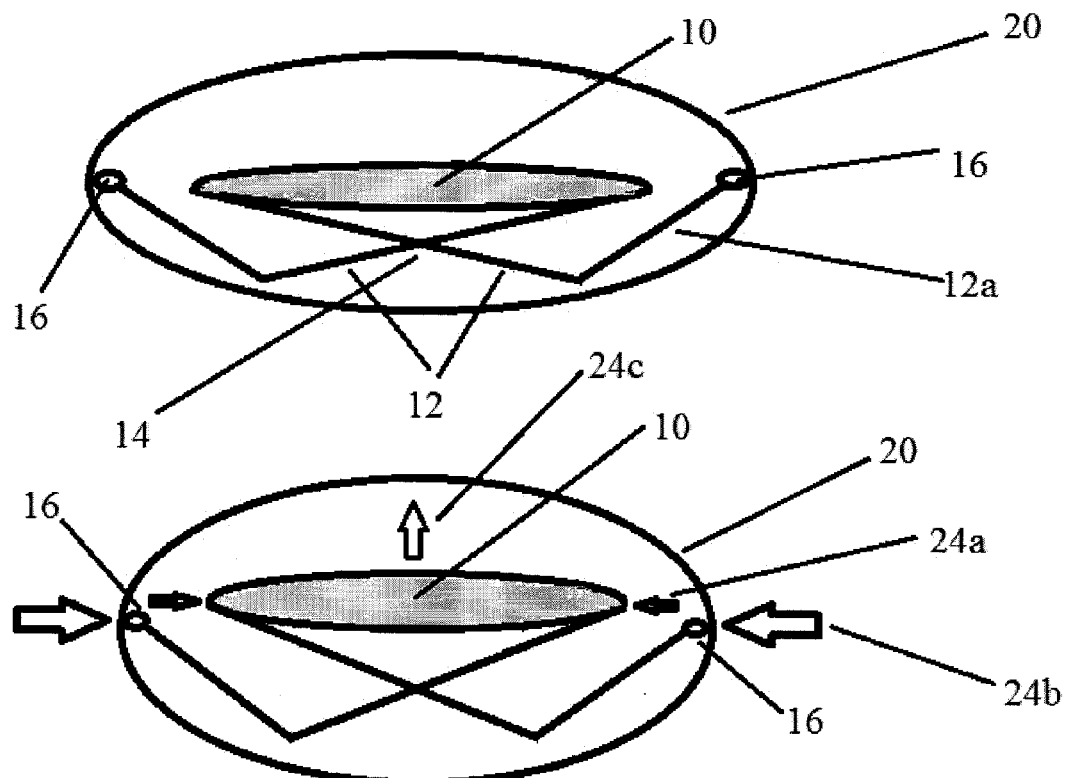
FIG. 1c depicts the essence of double accommodation due to deployment of resilient lazy tongs by enlarging their length and reducing their width.

FIG. 1a illustrates the top perspective view of the accordion double accommodating intraocular lens. This embodiment shows flexible optic 10, semi-rigid deployable single cell lazy tong structures 12, lazy tong struts 12a, lazy tong hinges 14, struts 14-2, flexible elastic haptics 16 and semi-rigid optic support plate 18. Semi-rigid haptic assembly 11 includes, preferably, three or four elastic haptics 16 configured as rings and three or four semi rigid deployable resilient lazy tongs 12, attached to semi-rigid optic support plate 18, configured as a single elastically flexible plate encompassing flexible optic 10. In this configuration the radial compression of capsular bag 20 as shown in FIGS. 1b and 1c by the contraction of ciliary muscles 25, axially moves and radially compresses flexible optic 10 in the lens and vice versa upon radial expansion of capsular bag 20. This is due to reduced pressure from ciliary muscles 25 and backward axial movement and decompression of flexible optic 10, due to action by resilient lazy tongs hinges 14, for double accommodations. Flexible optic 10 is suspended and connected to the deployable lazy tong structures 12 by a plurality of three or four lazy tong struts 12a. As shown in FIGS. 1b and 1c, the essence of double accommodation is that upon sphinctering pressure 24b applied by ciliary muscles 25 to the periphery of the capsular bag, the resilient lazy tongs deploy and move optic 10 forward (first accommodation action), while the reduction in the width of resilient lazy tongs 12 due to expansion produces pressure 24a on upper plate 18 encompassing optic 10 where it is touching upper plate 18. Thus, the optic moves forward and becomes more convex for more power as shown by arrow 24c in FIG. 1c.

Figure 2:
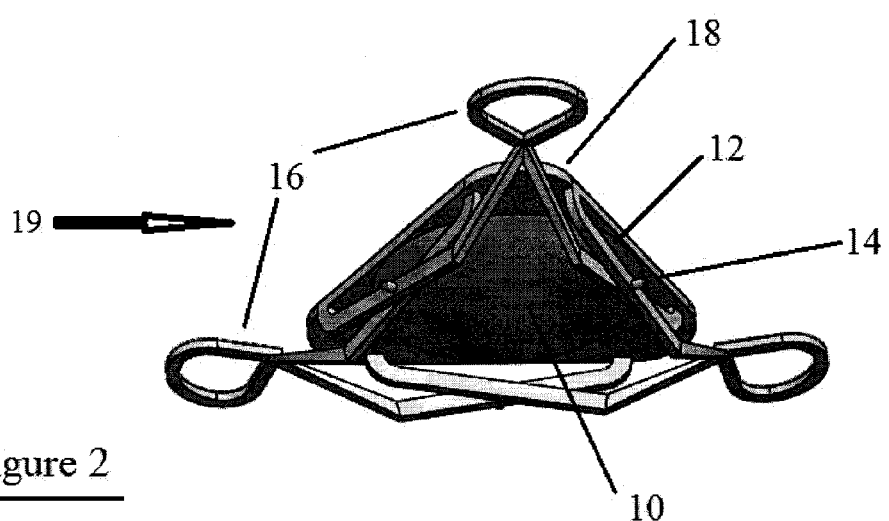
FIG. 2 depicts the bottom perspective view of the preferred accordion double accommodating intraocular lens.

FIG. 2 depicts the bottom perspective view of the accordion double accommodating intraocular lens. FIG. 2 shows flexible optic 10, semi-rigid deployable single cell lazy tong structure 12, lazy tong hinge 14, struts 14-2, flexible elastic haptics 16 and semi-rigid optic support plate 18.

Figure 3:
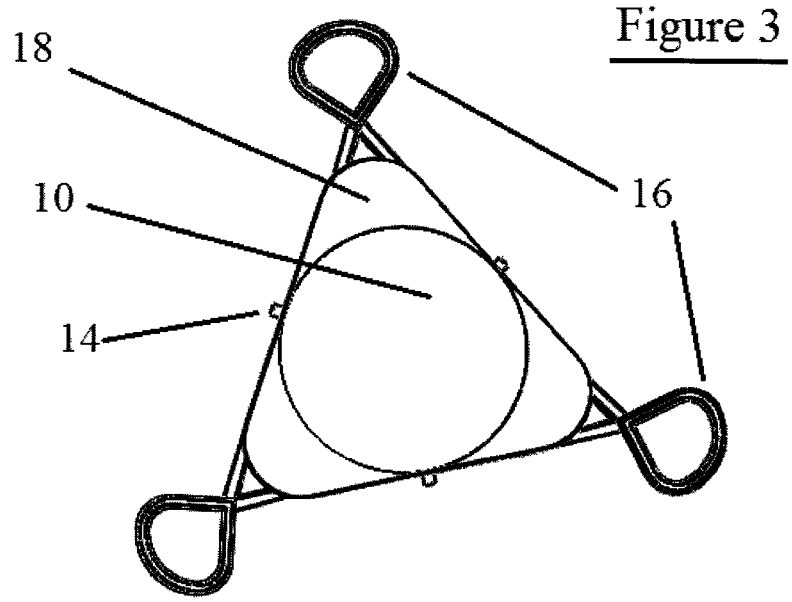
FIG. 3 displays the top view line drawing of the accordion double accommodating intraocular lens.

FIG. 3 displays the top view line drawing of the accordion double accommodating intraocular lens. FIG. 3 shows flexible optic 10, lazy tong hinge 14, struts 14-2, flexible elastic haptics 16, and semi-rigid optic support plate 18.

Figure 4:
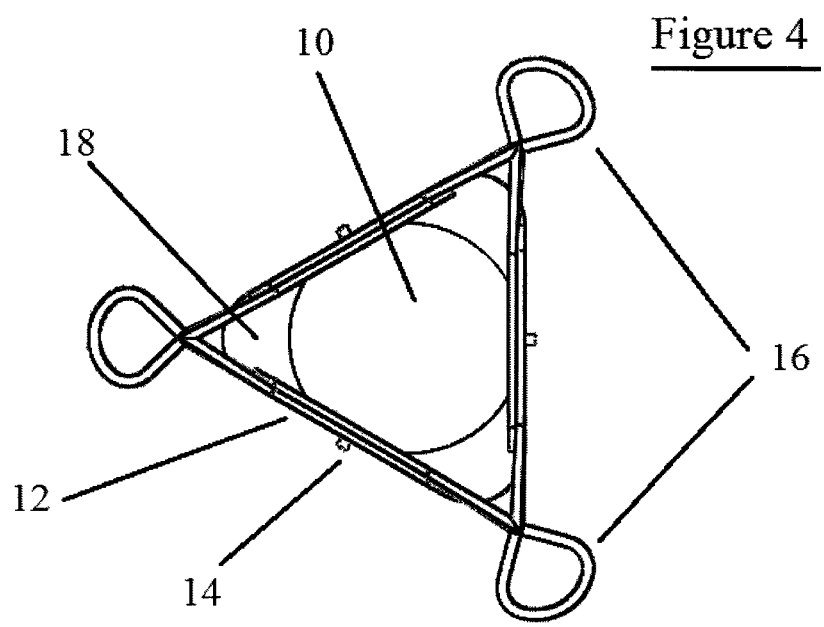
FIG. 4 depicts the bottom view line drawing of the accordion double accommodating intraocular lens.

FIG. 4 depicts the bottom view line drawing of the accordion double accommodating intraocular lens. FIG. 4 shows flexible optic 10, semi-rigid deployable single cell lazy tong structure 12, lazy tong hinge 14, struts 14-2, flexible elastic haptics 16 and semi-rigid optic support plate 18.

Figure 5:
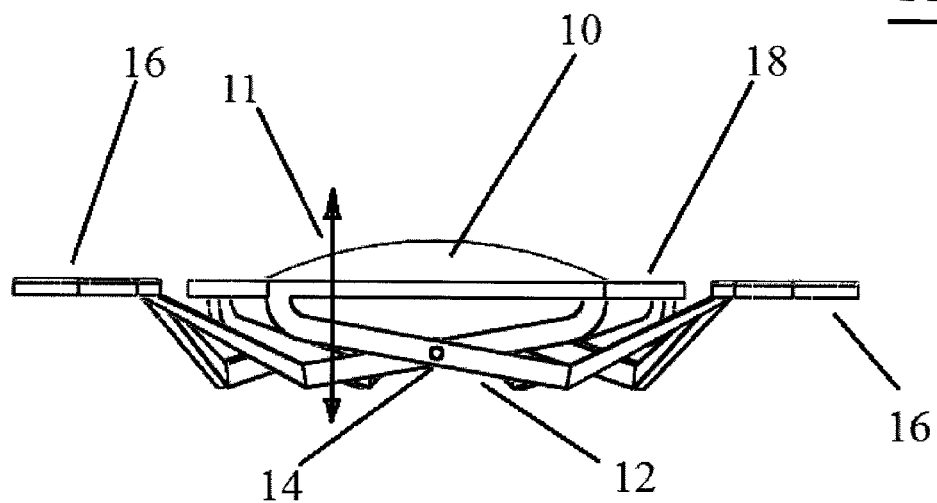
FIG. 5 depicts the side view line drawing of the accordion double accommodating intraocular lens.

FIG. 5 depicts the side view line drawing of the accordion double accommodating intraocular lens. FIG. 5 shows flexible optic 10, semi-rigid deployable single cell lazy tong structure 12, lazy tong hinge 14, struts 14-2, flexible elastic haptics 16 and semi-rigid optic support plate 18. Note that capsular peripheral pressure applied to haptics 16 forces the lazy tongs 12 to deploy in direction 11 and move optic 10 in direction 11 and squeeze optic 10 peripherally for double accommodation.

Figure 6:
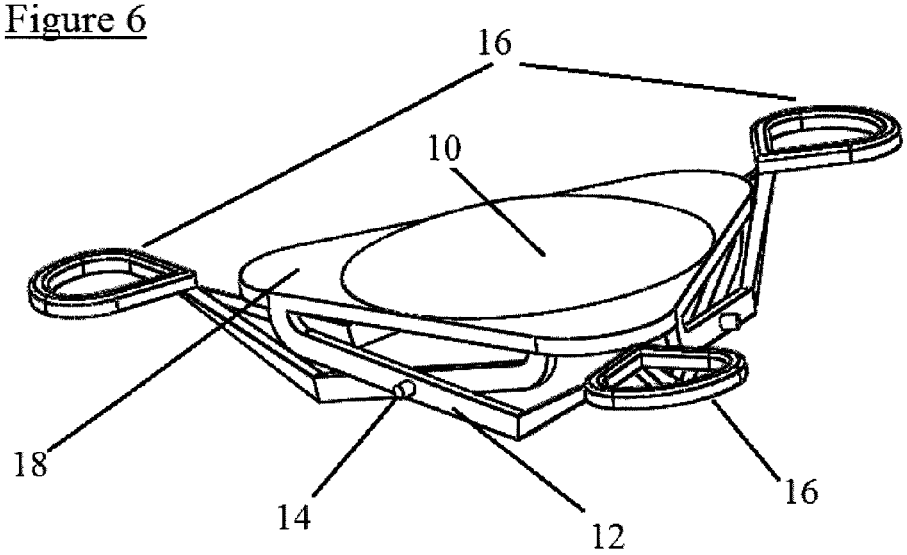
FIG. 6 depicts the perspective top view line drawing of the accordion double accommodating intraocular lens.

FIG. 6 depicts the perspective top view line drawing of the accordion double accommodating intraocular lens. FIG. 6 shows flexible optic 10, semi-rigid deployable single cell lazy tong structure 12, lazy tong hinge 14, struts 14-2, flexible elastic haptics 16, and semi-rigid optic support plate 18.

Figure 7:
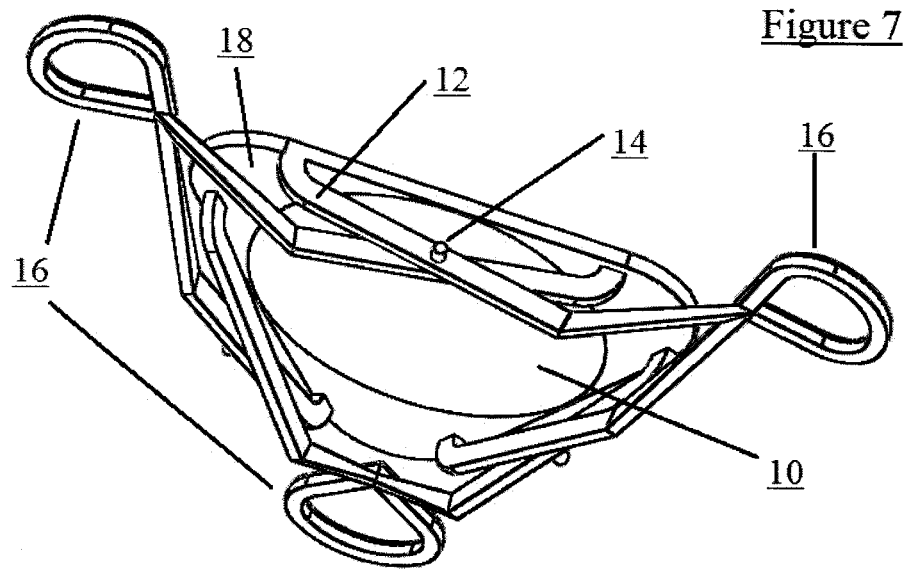
FIG. 7 depicts the perspective bottom view line drawing of the accordion double accommodating intraocular lens.

FIG. 7 depicts the perspective bottom view line drawing of the accordion double accommodating intraocular lens. FIG. 7 shows flexible optic 10, semi-rigid deployable single cell lazy tong structure 12, lazy tong hinge 14, struts 14-2, flexible elastic haptics 16 and semi-rigid optic support plate 18. FIGS. 2 through 7 function similar to the functionality of FIG. 1 and are shown for clarity.

Figure 8A:
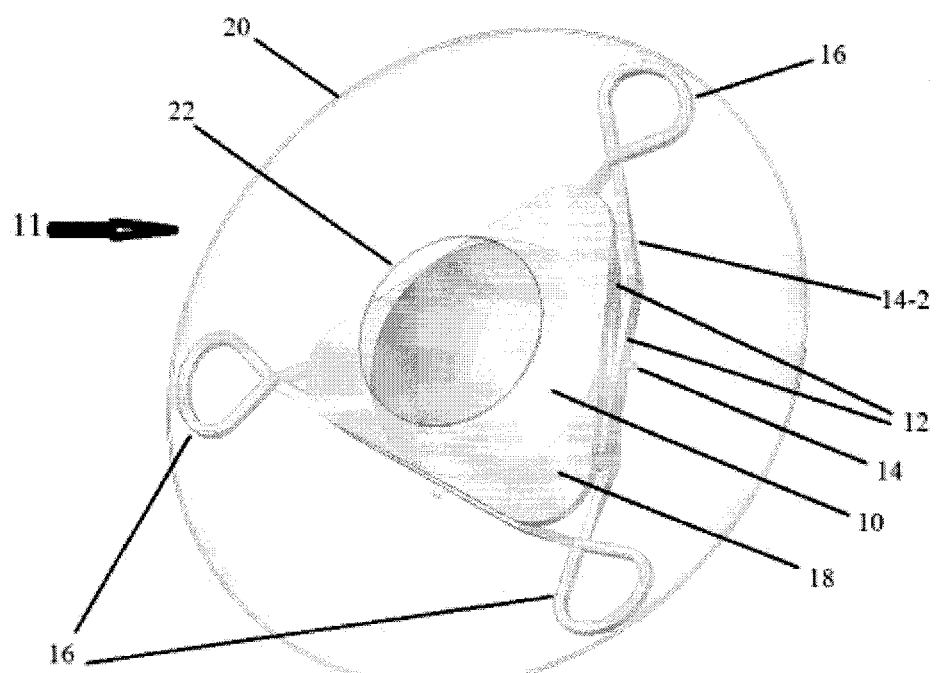
FIG. 8a depicts the perspective top view of the accordion double accommodating intraocular lens inside of a capsular bag.

FIG. 8a depicts the perspective top view of the accordion double accommodating intraocular lens inside of a capsular bag. FIG. 8a shows flexible optic 10, semi-rigid deployable single cell lazy tong structure 12, lazy tong hinge 14, struts 14-2, flexible elastic haptics 16, semi-rigid optic support plate 18, and capsular bag of the eye 20 showing its top opening 22 due to capsulorhexis. Within capsular bag 20 semi-rigid haptic assembly 11 includes, preferably, three or four ring haptics 16 and three or four deployable resilient lazy tongs 12, attached to a single elastically flexible plate 18 encompassing flexible optic 10. The radial compression of capsular bag 20 by the contraction of the ciliary muscles 25 (FIG. 1b) moves the haptics inward and causes resilient lazy tongs 12 to deploy axially and move optic 10 axially, and radially compresses 24a (FIG. 1c) flexible optic 10 in the lens. Additionally, upon radial expansion of capsular bag 20 and a pulling action or backward axial movement due to decompression of flexible optic 10, due to the resilient lazy tongs action, a continuous double accommodation takes place. Flexible optic 10 is suspended and connected to deployable lazy tong assembly 12 by a plurality of three or four resilient lazy tongs 12.

Figure 8B:
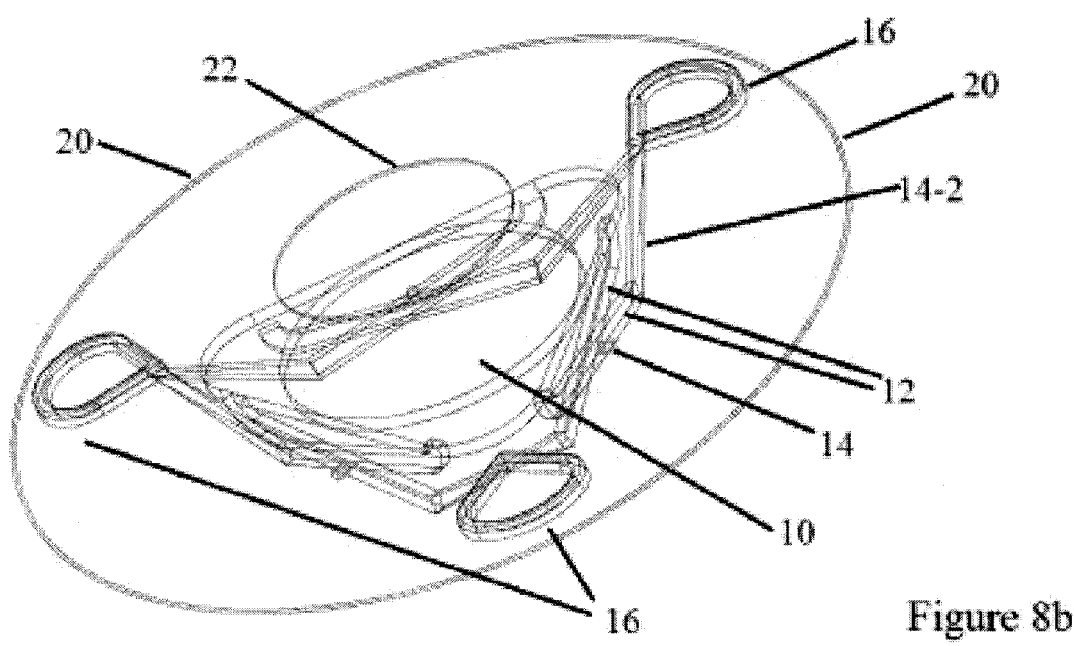
FIG. 8b depicts the top view line drawing of the accordion double accommodating intraocular lens inside of a capsular bag.

FIG. 8b depicts the top view line drawing of the accordion double accommodating intraocular lens inside of a capsular bag. FIG. 8b shows flexible optic 10, semi-rigid deployable single cell lazy tong structure 12, lazy tong hinge 14, struts 14-2, flexible elastic haptics 16, semi-rigid optic support plate 18 and capsular bag of the eye 20 showing its top opening 22 due to capsulorhexis. Double arrow 34 shows the deployment direction of optic 10.

Figure 9:
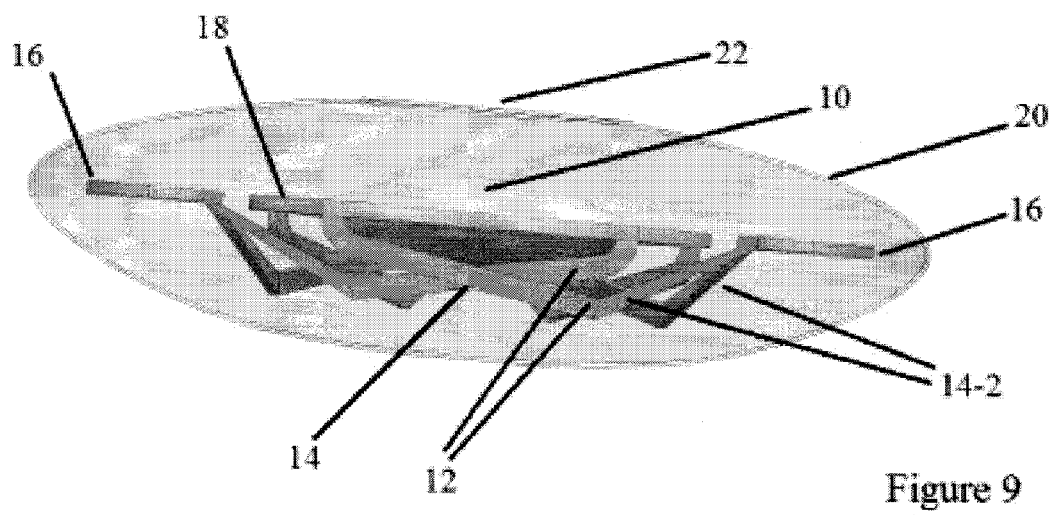
FIG. 9 depicts the perspective side view of the accordion double accommodating intraocular lens inside of a capsular bag.

FIG. 9 depicts the perspective side view of the accordion double accommodating intraocular lens with three (3) haptics in a capsular bag. FIG. 9 shows flexible optic 10, semi-rigid deployable single cell lazy tong structure 12, lazy tong hinge 14, struts 14-2, flexible elastic haptics 16, semi-rigid optic support plate 18 and capsular bag of the eye 20 showing its top opening 22 due to capsulorhexis. Note that element 40 depicts the direction of deployment of the DAIOL.

Figure 10:
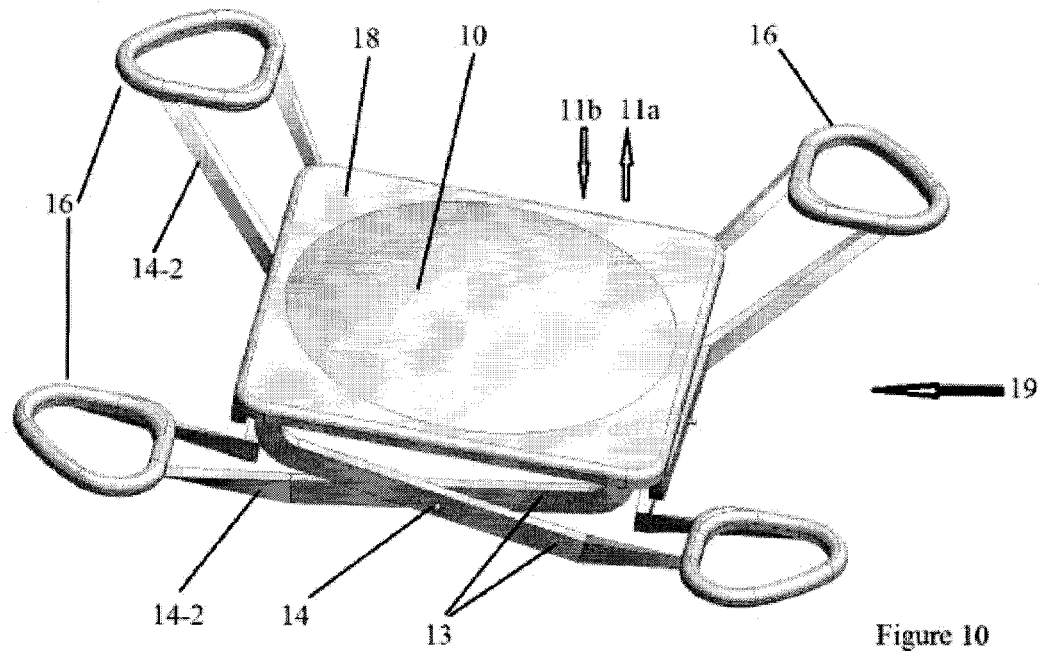
FIG. 10 illustrates the top perspective view of the accordion double accommodating intraocular lens with four (4) haptics.

FIG. 10 illustrates the top perspective view of the accordion double accommodating intraocular lens with four (4) haptics. Although, this disclosure shows embodiments with three (3) and four (4) haptics, any number of haptics in any configuration can be used and are specifically included. As in three (3) haptic assembly 11, four (4) haptic assembly 19 is configured so each haptic has a corresponding pair of resilient lazy tongs 13. FIG. 10 shows flexible optic 10, semi-rigid deployable single cell lazy tong structure 13, lazy tong hinge 14, struts 14-2, flexible elastic haptics 16 and semi-rigid optic support plate 18. Each deployable lazy tong 13 is attached to single elastically flexible plate 18 encompassing flexible optic 10. The movement of the upper plate containing the optic is in shown in FIG. 10 as 11a or 11b direction. As shown in FIGS. 1b and 1c radial compression of capsular bag 20 by the contraction of ciliary muscles 25 axially moves 24c and radially compresses 24a flexible optic 10 in capsule 20. Additionally, upon radial expansion of capsular bag 20, backward axial movement and decompression of flexible optic 10, due to the resilient lazy tongs action, provides for continuous double accommodations. In FIG. 10, flexible optic 10 is suspended and connected to deployable lazy tong assembly 19 by three or four resilient lazy tongs 13.

Figure 11:
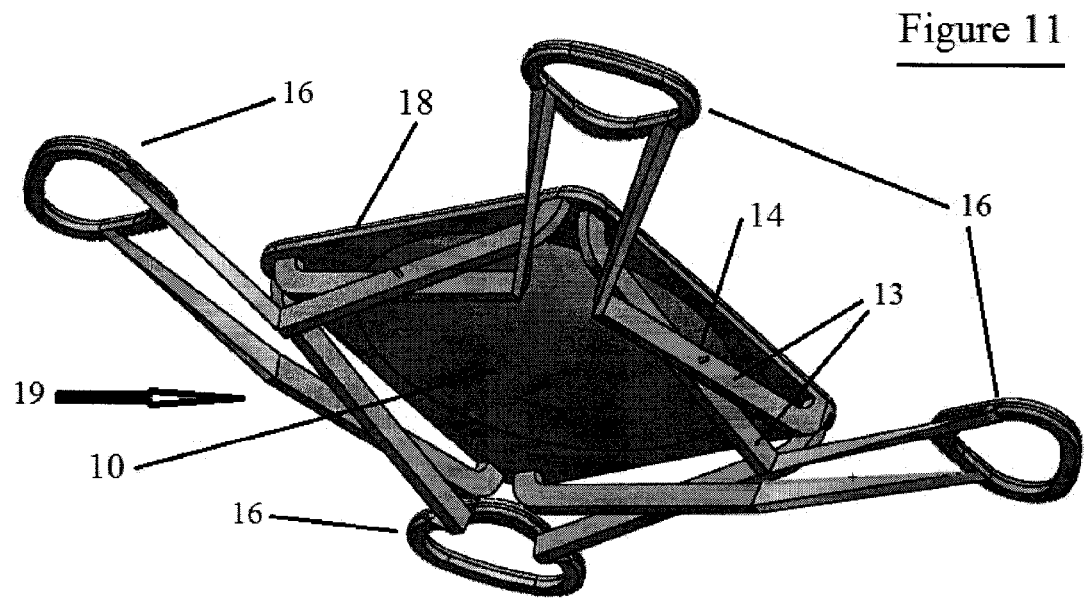
FIG. 11 depicts the bottom perspective view of the accordion double accommodating intraocular lens of FIG. 10.

FIG. 11 depicts the bottom perspective view of the accordion double accommodating intraocular lens of FIG. 10. This figure shows the preferred embodiment of the presently claimed invention with a four (4) haptics assembly 19 showing flexible optic 10, semi-rigid deployable single cell lazy tong structure 13, lazy tong hinge 14, struts 14-2, flexible elastic haptics 16, and semi-rigid optic support plate 18.

Figure 12:
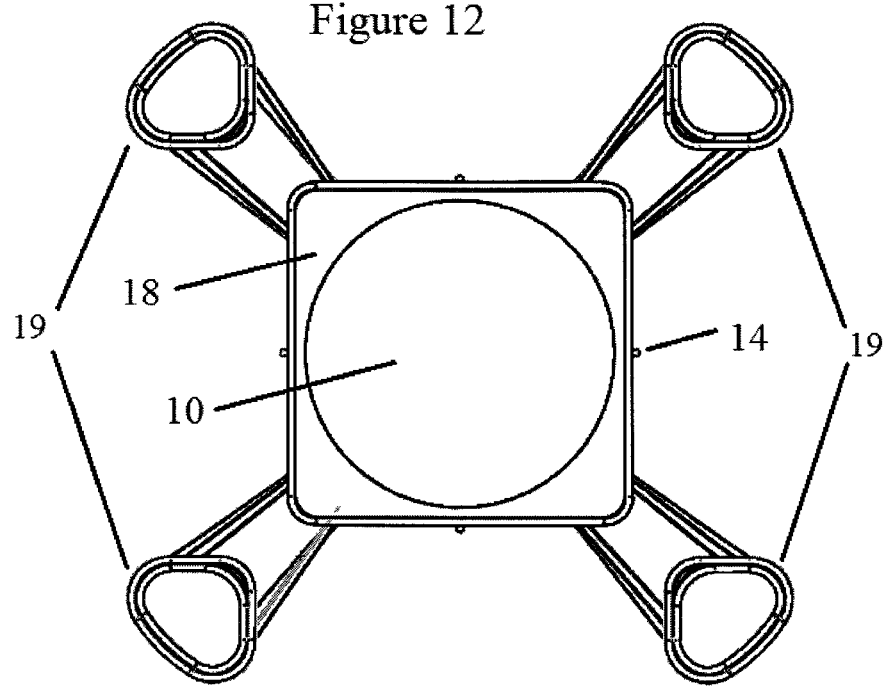
FIG. 12 displays the top view line drawing of the accordion double accommodating intraocular lens of FIG. 10.

FIG. 12 displays the top view line drawing of the accordion double accommodating intraocular lens of FIG. 10. FIG. 12 shows a four (4) flexible elastic haptics assembly 19 showing flexible optic 10, lazy tong hinge 14, struts 14-2, flexible elastic haptics 16, and semi-rigid optic support plate 18.

Figure 13:
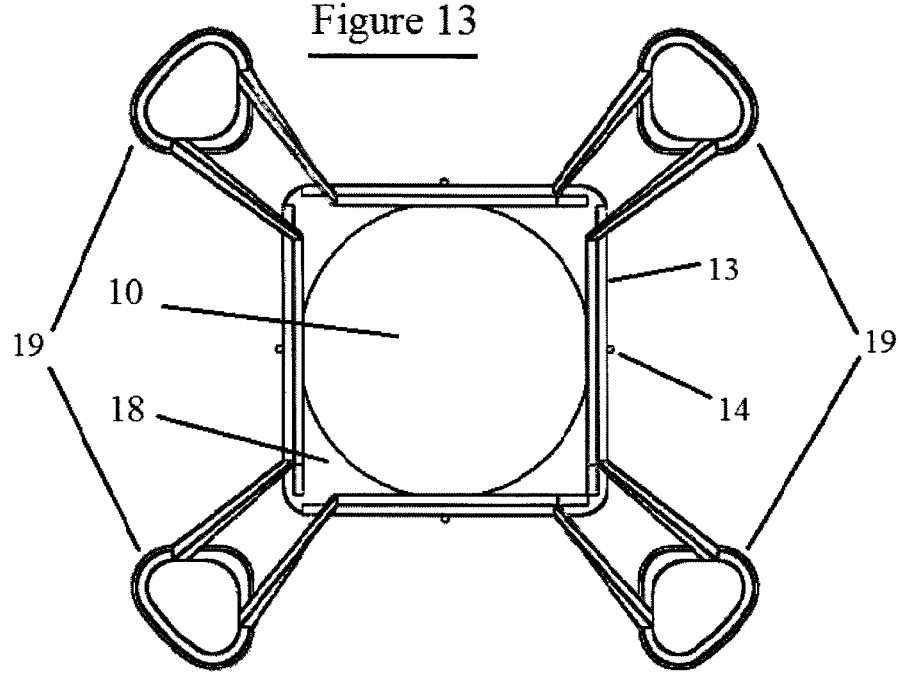
FIG. 13 illustrates the bottom view line drawing of the accordion double accommodating intraocular lens of FIG. 10.

FIG. 13 illustrates the bottom view line drawing of the accordion double accommodating intraocular lens of FIG. 10. FIG. 13 shows a four (4) elastic haptic assembly 19 showing flexible optic 10, semi-rigid deployable single cell lazy tong structure 13, lazy tong hinge 14, struts 14-2, flexible elastic haptics 16, and semi-rigid optic support plate 18.

Figure 14:
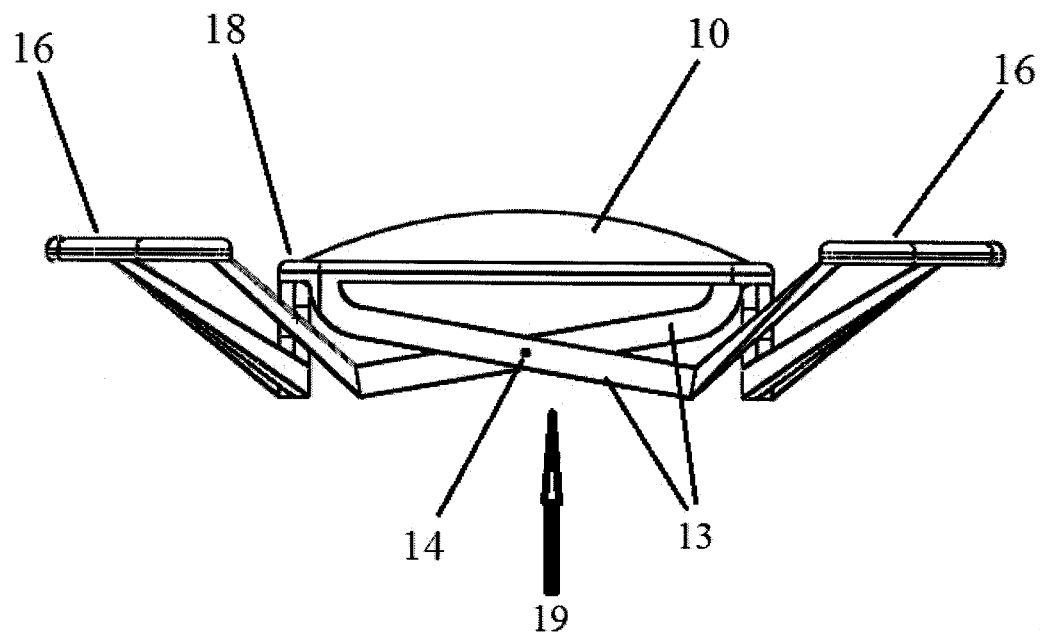
FIG. 14 depicts the side view line drawing of the accordion double accommodating intraocular lens of FIG. 10.

FIG. 14 depicts the side view line drawing of the accordion double accommodating intraocular lens of FIG. 10. FIG. 14 shows a four (4) elastic haptic assembly 19 showing flexible optic 10, semi-rigid deployable single cell lazy tong structure 13, lazy tong hinge 14, struts 14-2, flexible elastic haptics 16, and semi-rigid optic support plate 18. Note that capsular peripheral pressure applied to haptics 16 forces lazy tongs 13 to deploy in the direction of optic axis and move optic 10 in the direction of optic axis (element 11 in FIG. 5) and squeeze optic 10 peripherally for double accommodation.

Figure 15:
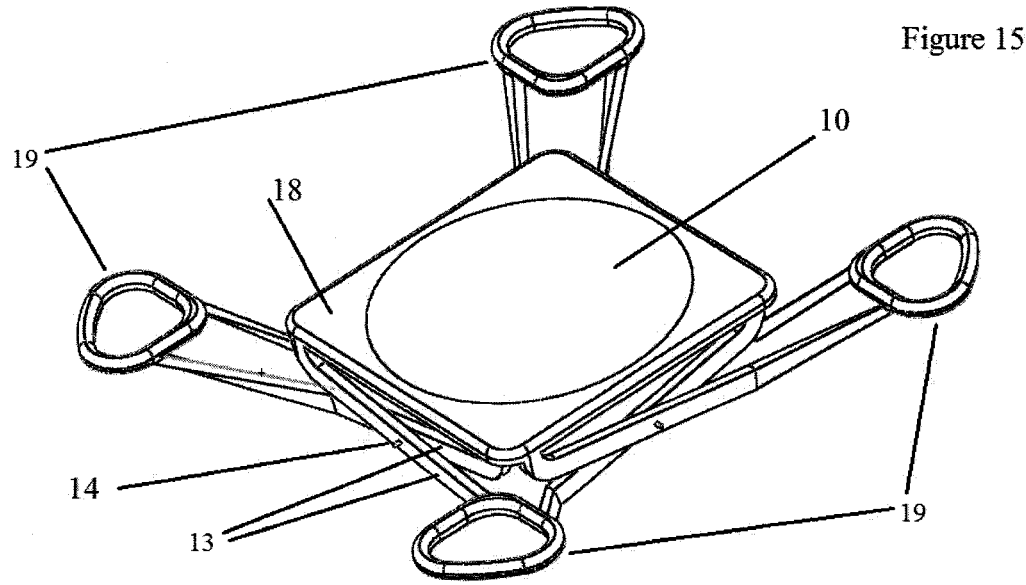
FIG. 15 depicts the perspective top view line drawing of the accordion double accommodating intraocular lens of FIG. 10.

FIG. 15 depicts the perspective top view line drawing of the accordion double accommodating intraocular lens of FIG. 10. FIG. 15 shows a four (4) elastic haptic assembly 19 showing flexible optic 10, semi-rigid deployable single cell lazy tong structure 13, lazy tong hinge 14, struts 14-2, flexible elastic haptics 16, and semi-rigid optic support plate 18.

Figure 16:
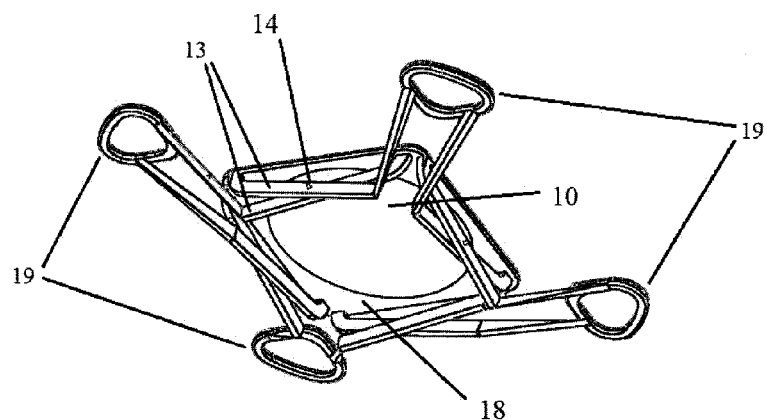
FIG. 16 depicts the perspective bottom view line drawing of the accordion double accommodating intraocular lens of FIG. 10.

FIG. 16 depicts the perspective bottom view line drawing of the accordion double accommodating intraocular lens of FIG. 10. FIG. 16 shows a four (4) elastic haptic assembly 19 showing flexible optic 10, semi-rigid deployable single cell lazy tong structure 13, lazy tong hinge 14, struts 14-2, flexible elastic haptics 16, and semi-rigid optic support plate 18.

Figure 17A:
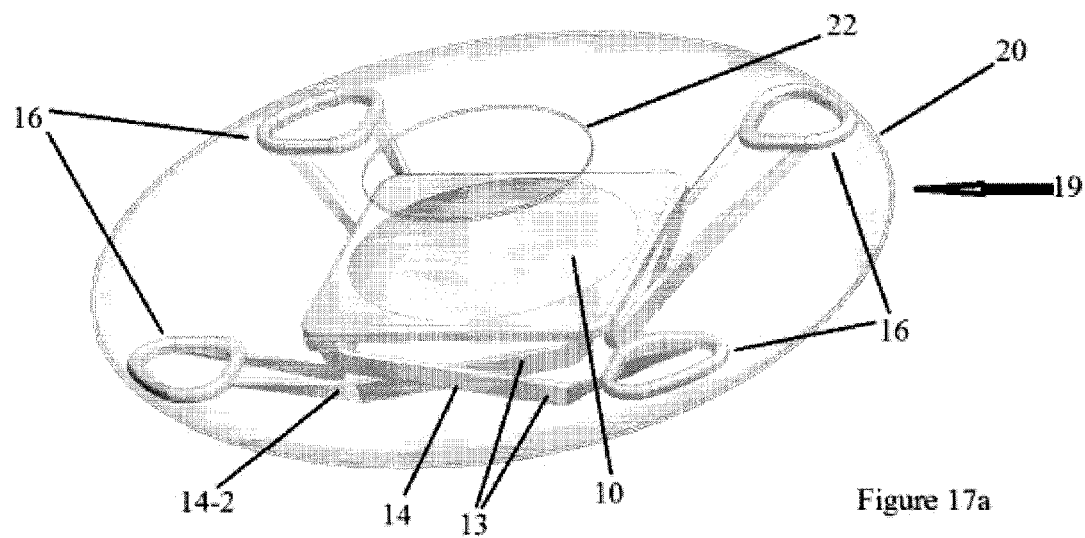
FIG. 17a depicts the perspective top view of the accordion double accommodating intraocular lens inside of a capsular bag.

FIG. 17a depicts the perspective top view of the accordion double accommodating intraocular lens in a capsular bag. In this embodiment there is a four (4) haptic assembly 19 with four (4) elastic haptics 16, flexible optic 10, semi-rigid deployable single cell lazy tong structure 13, lazy tong hinge 14, struts 14-2, flexible elastic haptics 16, semi-rigid optic support plate 18, and capsular bag of the eye 20 showing its top opening 22 due to capsulorhexis. Preferably, the semi-rigid haptic assembly 11 and 19 contains three or four ring haptics 16 and three or four deployable resilient lazy tongs 12, attached to single elastically flexible plate 18 encompassing a flexible optic 10. Accordingly, radial compression of capsular bag 20, as shown in FIGS. 1b and 1c, by the contraction of ciliary muscles 25 in FIG. 1b, axially moves and radially compresses flexible optic 10, as shown in FIGS. 1b and 1c. Upon radial expansion of capsular bag 20 and backward axial movement, as shown in FIGS. 1b and 1c, causes decompression of optic 10, and moving back due to the lazy tong action, for double accommodations. Flexible optic 10 is suspended and connected to the deployable lazy tong assembly by a plurality of three or four resilient lazy tongs 13.

Figure 17B:
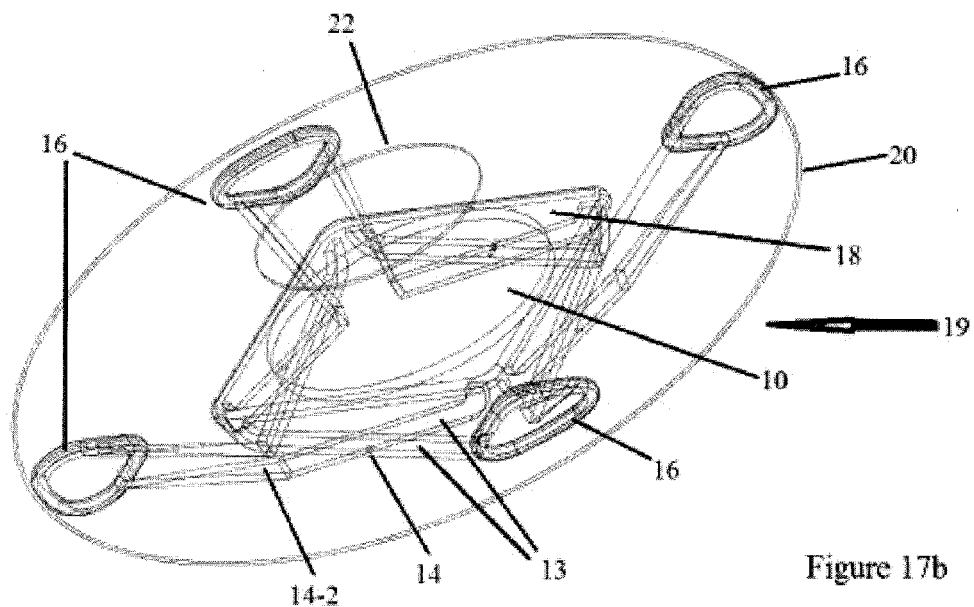

FIG. 17b depicts the top view line drawing of the accordion double accommodating intraocular lens of FIG. 17a. FIG. 17b shows four (4) elastic haptics 16 in a four (4) haptic assembly 19 with flexible optic 10, semi-rigid deployable single cell lazy tong structure 13, lazy tong hinge 14, struts 14-2, flexible elastic haptics 16, semi-rigid optic support plate 18, and capsular bag of the eye 20 showing its top opening 22 due to capsulorhexis.

Figure 18:
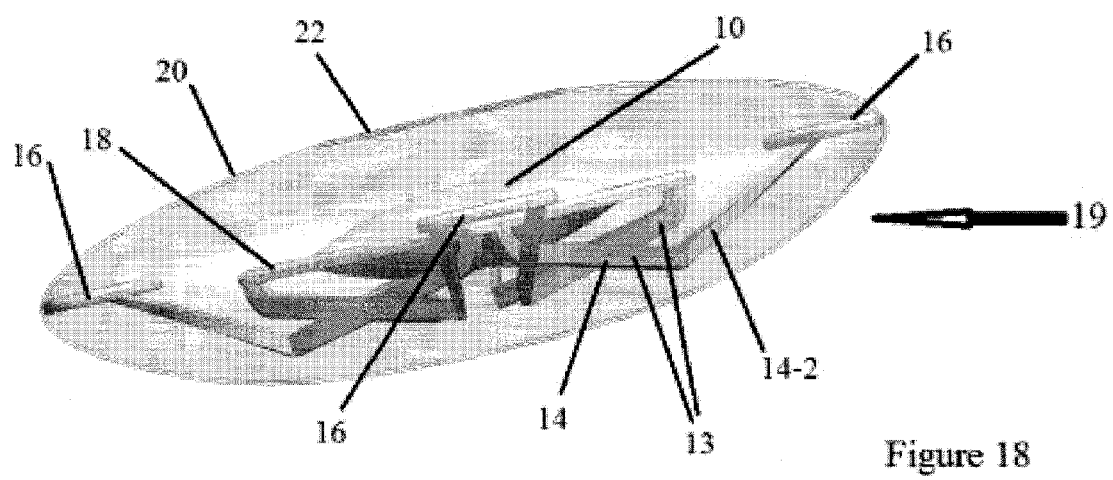

FIG. 18 depicts the perspective side view of the accordion double accommodating intraocular lens of FIG. 17a. FIG. 18 shows four (4) elastic haptics 16 in a four (4) haptic assembly 19 with flexible optic 10, semi-rigid deployable single cell lazy tong structure 13, lazy tong hinge 14, struts 14-2, flexible elastic haptics 16, semi-rigid optic support plate 18, and capsular bag of the eye 20 showing its top opening 22 due to capsulorhexis.

Figure 19A:
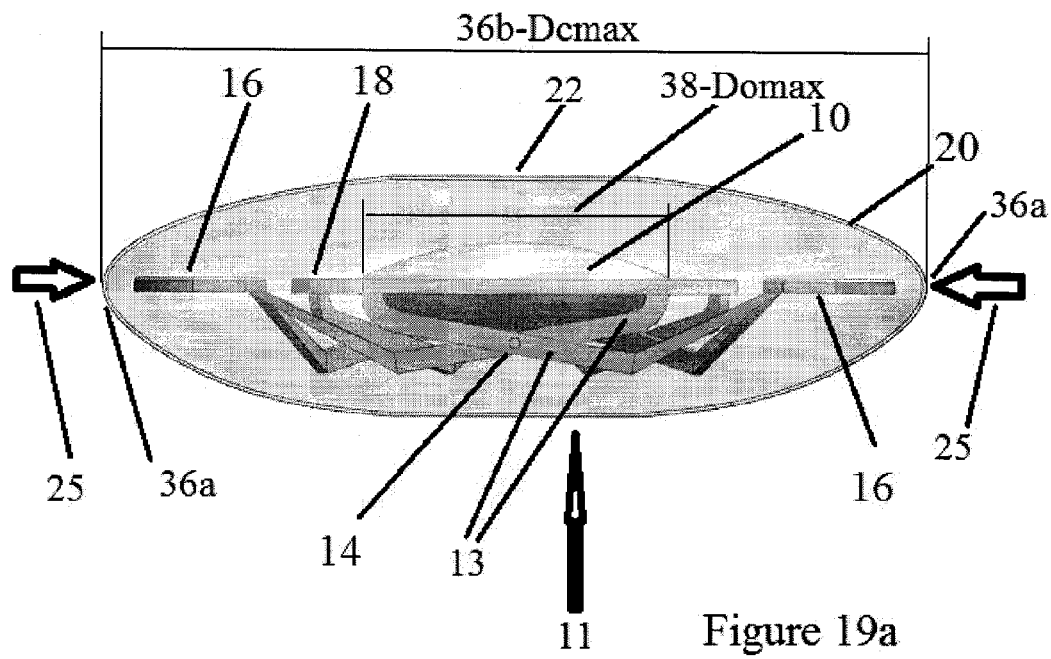
FIG. 19a is the DAIOL with three (3) haptics housed inside the capsular bag in its initial reference state before accommodation.
Figure 19B:
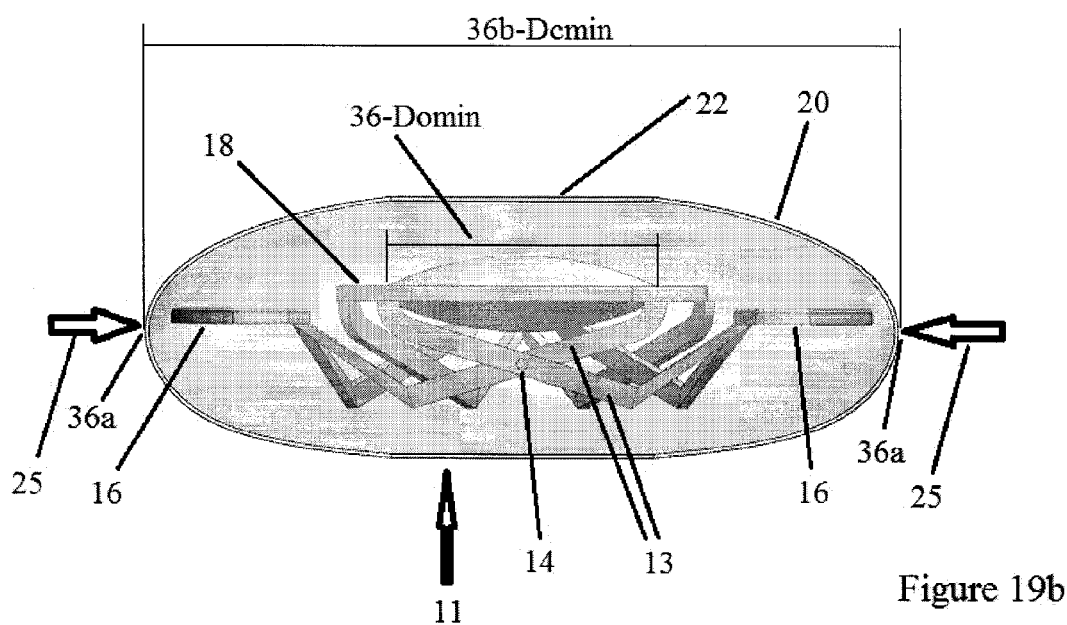
FIG. 19b is the DAIOL with three (3) haptics housed inside the capsular bag in its maximum deployment configuration.

FIGS. 19a and 19b depict minimum and maximum deployment configurations of the accordion lens for a three (3) haptic assembly 11.

FIG. 19a shows a three (3) haptic assembly 11 with flexible haptics 16 fitted inside capsular bag 20 through capsular opening 22. At this stage, ciliary muscles 25 are in their natural state and not compressing the capsule on capsule equator 36a. Thus, the optic is at its minimum deployment and no accommodation is occurring. Thus, the diameter of optic 38 is at its maximum $Do_{max}$ and the diameter of capsule 36b is also at its $Dc_{max}$.

FIG. 19b shows a three (3) haptic assembly 11 with flexible haptics 16 fitted inside capsular bag 20 through capsular opening 22. As ciliary muscles 25 contract and apply peripheral pressure on capsule equator 36a, which causes the diameter of the capsule 38 to decrease progressively to $Dc_{min}$ and increase back again during double accommodation. This causes accordion lens lazy tong mechanism 13 and hinges 14 to deploy within capsule 20 for accommodation due to axial movement of optic 10. In addition, this transmits some of the pressure through elastic haptics 16 to apply peripheral pressure also to the top plate 18 containing optic 10 for compression type accommodation, thus creating double accommodations. In this configuration, the optic will be at its maximum accommodation state with a minimum diameter of $Do_{min}$.

Figure 20A:
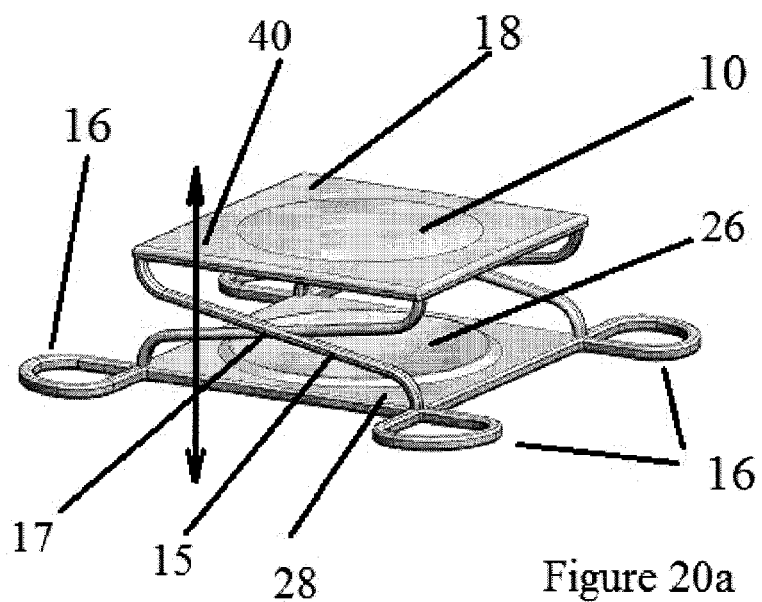
FIG. 20a is an embodiment of the DAIOL with four (4) elastic haptics with dual optics that has a high-powered anterior optic supported by a top semi-rigid plate and joined to a rear minus-powered optic supported by a semi-rigid bottom plate by the lazy tong structures and hinge.

FIG. 20a is another embodiment of the presently claimed invention with 4 elastic haptics 16 with dual optics 10 and 26 that has a high-powered anterior optic 10 supported by a top semi-rigid plate 18 and joined to a rear minus-powered optic 26 supported by a semi-rigid bottom plate 28 by the lazy tong structures and hinge 15 and 17. Note that the direction of deployment is shown by 40.

Figure 20B:
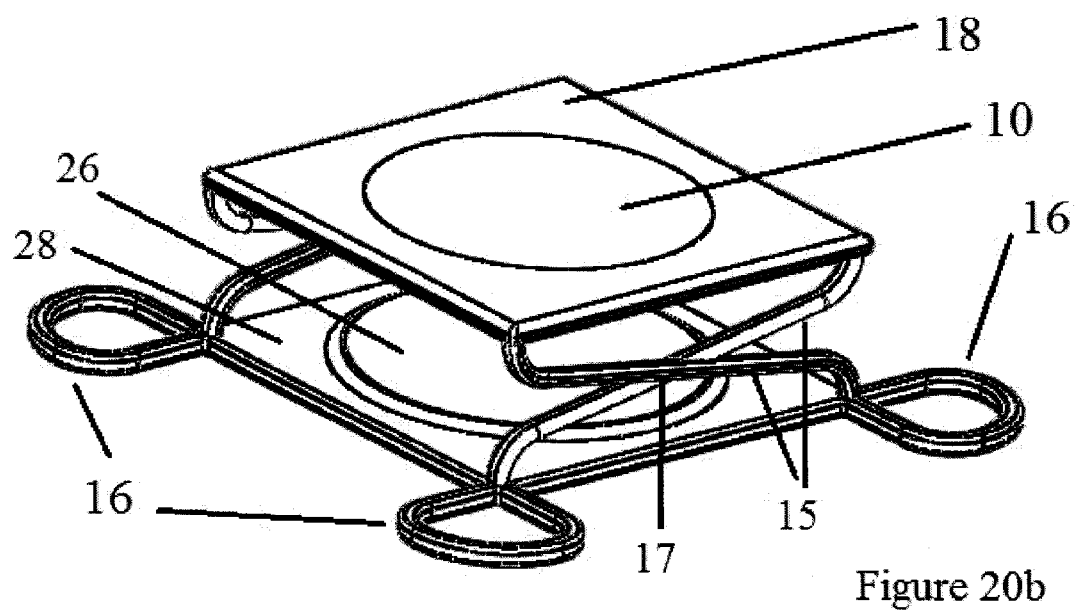
FIG. 20b is another embodiment of the DAIOL with four (4) elastic haptics with dual optics that has a high-powered anterior optic supported by a top semi-rigid plate and joined to a rear minus-powered optic supported by a semi-rigid bottom plate by the lazy tong structures and hinge.

FIG. 20b is a line drawing embodiment of the presently claimed invention according to FIG. 20a with four (4) elastic haptics 16 with dual optics 10 and 26 that has a high-powered anterior optic 10 supported by a top semi-rigid plate 18 and joined to a rear minus-powered optic 26 supported by a semi-rigid bottom plate 28 by the lazy tong structures and hinge 15 and 17, respectively.

Figure 21A:
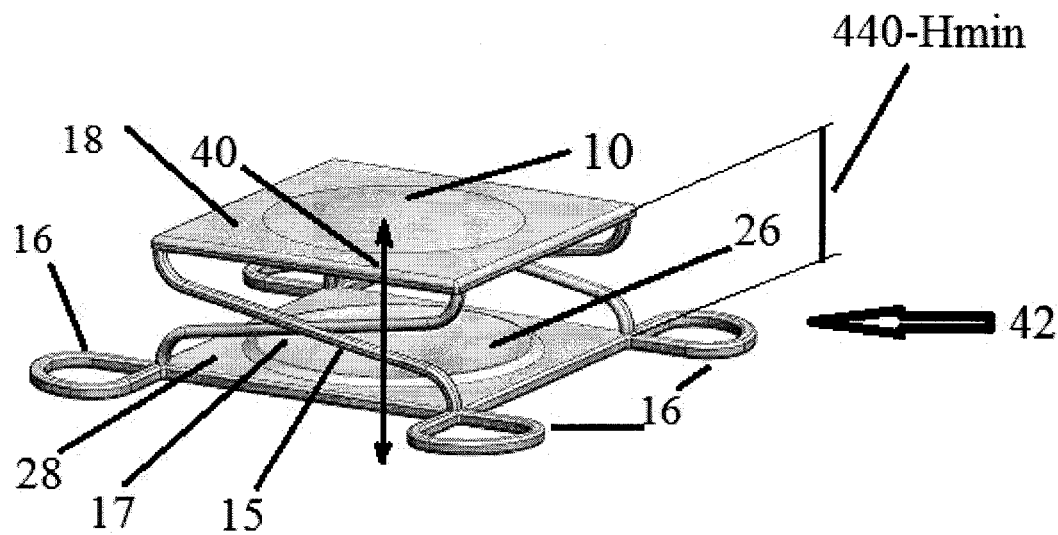
FIG. 21a depicts a double optic accordion DAIOL at its minimum deployment state, showing how it deploys to change the distance between the high-powered anterior optic supported by a top semi-rigid plate and joined to a rear minus-powered optic supported by a semi-rigid bottom plate by the lazy tong structures and hinge.

FIG. 21a depicts the proposed double optic accordion DAIOL at its minimum deployment state with an effective height of $H_{min}$, showing how it deploys to change the distance between the high-powered anterior optic 10 supported by a top semi-rigid plate 18 and joined to a rear minus-powered optic 24 supported by a semi-rigid bottom plate 26 by the lazy tong structures and hinge 15 and 17, respectively.

FIG. 21a, depict how double optic accordion DAIOL 42 deploys to change the height H 44 between the high-powered anterior optic 10 supported by a top semi-rigid plate 18 and joined to a rear minus-powered optic 26 supported by a semi-rigid bottom plate 28 by lazy tong structures 15 and lazy tong hinge 17. In all of the above figures, the action of the systems is that the semi-rigid haptic assemblies 11 or 19 include, preferably, three or four ring haptics 16 and three or four deployable resilient lazy tongs 12, attached to a single elastically flexible optic plate 18 encompassing a flexible optic 10. Radial compression of capsular bag 20 by the contraction of ciliary muscles 25 axially moves 44 in the direction 40 and radially compresses flexible optic 10 in the lens. Additionally, upon radial expansion of capsular bag 20 and backward axial movement causes decompression of optic 10, due to the resilient lazy tongs action, for double accommodations. Flexible optic 10 is suspended and connected to deployable lazy tong assemblies 11 or 19 by three or four resilient lazy tongs 15.

Figure 21B:
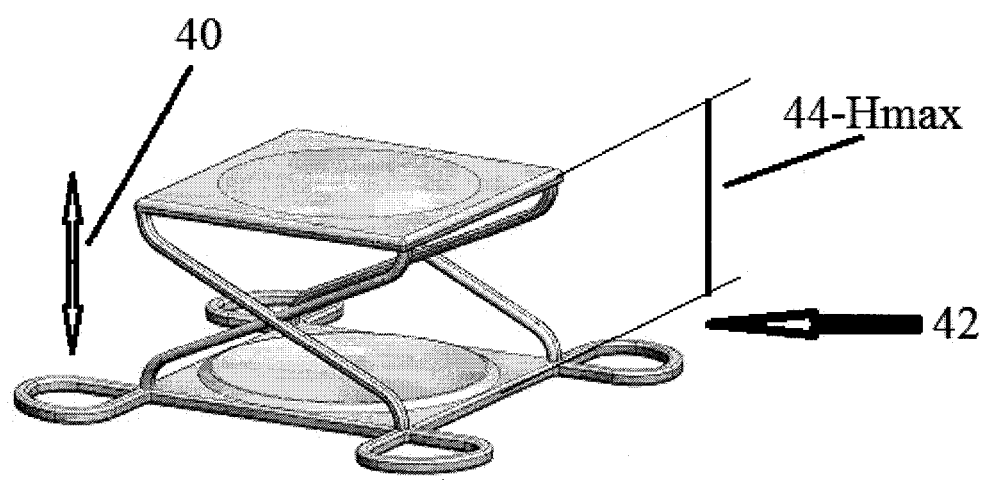
FIG. 21b depicts final maximum deployment state of the double optic accordion DAIOL to change the distance between the high-powered anterior optic supported by a top semi-rigid plate and joined to a rear minus-powered optic supported by a semi-rigid bottom plate by the lazy tong structures and hinge.

FIG. 21b depicts final maximum deployment state of the proposed double optic accordion DAIOL with a height $H_{max}$ 44, to change the distance between the high-powered anterior optic 10 supported by a top semi-rigid plate 18 and joined to a rear minus-powered optic 26 supported by a semi-rigid bottom plate 28 by the lazy tong assembly 42 and structures and hinge 15 and 17, respectively. Note that element 40 depicts the direction of deployment.

Figure 22A:
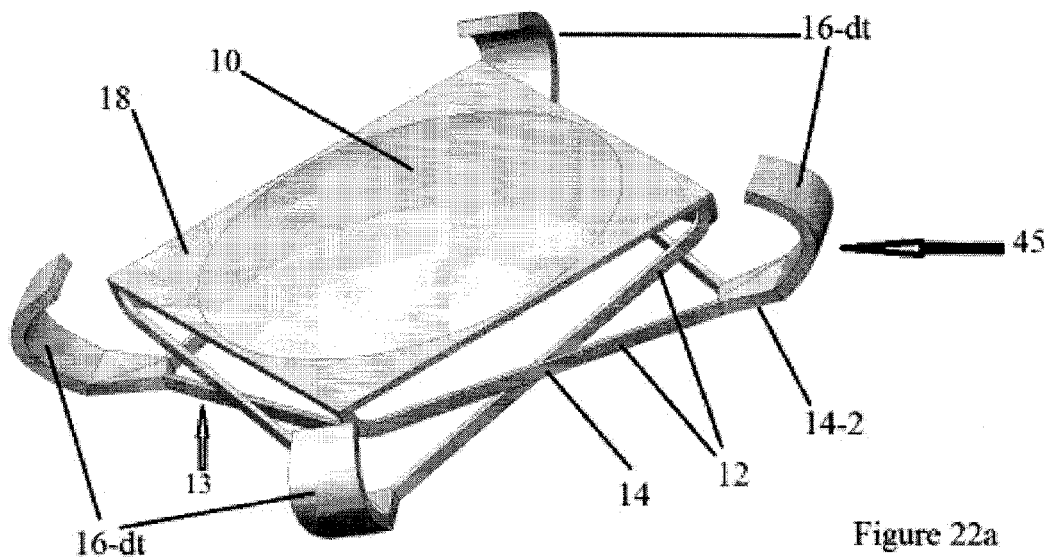
FIG. 22a Illustrates the top perspective view of the accordion double accommodating intraocular lens with three (3) discrete tubular haptics.

FIG. 22a Illustrates the top perspective view of the accordion double accommodating intraocular lens with discrete tubular haptics 16-dt. This embodiment shows flexible optic 10, semi-rigid deployable single cell lazy tong structure 13, with resilient lazy tongs 12, lazy tong hinges 14, struts 14-2, flexible elastic tubular haptics 16-dt and semi-rigid optic support plate 18. Semi-rigid tubular haptic assembly 45 includes, preferably, three or four ring haptics 21 and three or four deployable resilient lazy tongs 12, attached to a single elastically flexible plate 18 encompassing a flexible optic 10. Radial compression 28 of capsular bag 20 by the contraction of ciliary muscles 25 axially moves and radially compresses flexible tubular optic 10 in the lens. Additionally, upon radial expansion of capsular bag 20 and backward axial movement causes decompression of flexible optic 10, due to the resilient lazy tongs action, for double accommodations. Flexible optic 10 is suspended and connected to deployable lazy tong assembly 13 by a plurality of three or four resilient lazy tongs 12.

Figure 22B:
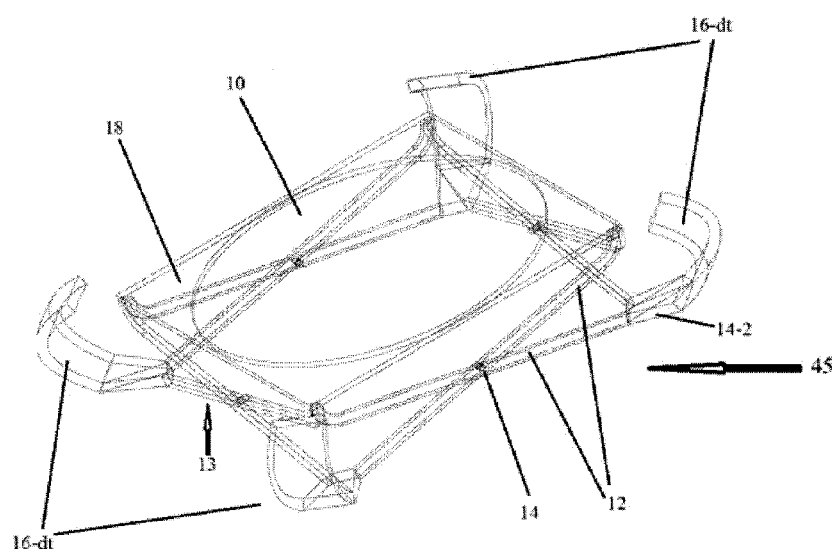

FIG. 22*b* Illustrates the line drawing of the top perspective view of the accordion double accommodating intraocular lens of FIG. 22*a*. This embodiment shows flexible optic 10, semi-rigid deployable single cell lazy tong structure 13, with resilient lazy tongs 12, lazy tong hinges 14, flexible elastic tubular haptics 16-*dt* and semi-rigid optic support plate 18. Semi-rigid tubular haptic assembly 45 includes, preferably, three or four tubular haptics 16-*dt* and three or four deployable resilient lazy tongs 12, attached to a single elastically flexible plate 18 encompassing a flexible optic 10. Radial compression of capsular bag 20 by the contraction of ciliary muscles 25 axially moves and radially compresses flexible tubular optic 10 in the lens. Additionally, upon radial expansion of capsular bag 20 and backward axial movement causes decompression of flexible optic 10, due to the resilient lazy tongs action, for double accommodations. Flexible optic 10 is suspended and connected to deployable lazy tong assembly 13 by a plurality of three or four resilient lazy tongs 12.

The preferred method for inserting the DAIOL into capsular bag 20 is accomplished by the steps of: an ultrasound probe used to break the opacified lens into tiny pieces; and removing the tiny pieces through a small incision in the cornea (phacoemulsification). An accommodating lens rather than a standard intraocular lens is then inserted through the incision into capsular bag 20. The DAIOL is pre-folded into a specifically designed lens folder and through the small corneal incision is placed into the capsular bag 20. Due to the unique properties of the lens, the DAIOL assumes a central fixation on the bag.

There is moderate quality evidence that study participants who received accommodative IOLs had a small gain in near visual acuity after six months. There is some evidence that distance visual acuity with accommodative lenses may be worse after 12 months. This is due to many factors, one being the unstable properties of the current intraocular lens currently in the market. Factors involved, include variable positioning and post-operative capsular fibrosis.

Due to the unique stabilization property of the DAIOL and the unique and sensitive actuating accordion mechanism for accommodation, the lens position and the diopter power is enhanced and maintained. Thus, the stabilization of the distance acuity as well as maintaining a high degree of accommodation is maintained.

Although the presently claimed invention has been described in detail with particular reference to these preferred embodiments, other embodiments can achieve the same results. Variations and modifications of the presently claimed invention will be obvious to those skilled in the art and it is intended to cover in all such modifications and equivalents. The entire disclosures of all references, applications, patents, and publications cited above, are hereby incorporated by reference.

What is claimed is:

1. A double accommodating intraocular accordion lens system (DAIOL) for insertion into a capsular bag of an eye, comprising:
   an assembly of deployable lazy tongs and elastic haptics comprising a plurality of haptics and a plurality of hinged lazy tongs, attached to a plate encompassing an optic, wherein the deployed assembly of lazy tongs and elastic haptics are configured to axially move the optic in a direction comprising a first mode of accommodation and to peripherally compress the optic to bulge it out and further axially move the optic in the direction comprising a second mode of accommodation in response to ciliary muscle action.

2. The double accommodating intraocular accordion lens system of claim 1 wherein each haptic comprises a ring haptic.

3. The double accommodating intraocular accordion lens system of claim 1 wherein the haptic assembly comprises a rigid assembly.

4. The double accommodating intraocular accordion lens system of claim 1 wherein the plurality of hinged lazy tongs comprise accordion lazy tongs.

5. The double accommodating intraocular accordion lens system of claim 4 wherein the plurality of haptics are configured to be disposed within a capsular bag to move in conjunction with radial compression and radial expansion of the capsular bag, resulting in the axial movement and radial compression of the optic.

6. The double accommodating intraocular accordion lens system of claim 1 wherein the optic comprises a single flexible optic.

7. The double accommodating intraocular accordion lens system of claim 1 wherein the optic is configured to be suspended in a capsular bag and connected to the plurality of hinged lazy tongs by a plurality of lazy tong struts.

8. The double accommodating intraocular accordion lens system of claim 1 wherein each haptic comprises a tubular haptic.

9. The double accommodating intraocular accordion lens system of claim 1 wherein the haptic assembly comprises an elastic haptic assembly.

10. The double accommodating intraocular accordion lens system of claim 1 wherein the plurality of hinged lazy tongs comprise scissor lazy tongs.

* * * * *